United States Patent [19]
Piscitelli et al.

[11] Patent Number: 6,064,720
[45] Date of Patent: May 16, 2000

[54] MAGNETIC SUPPORT FOR REMOVABLE ANTISCATTER GRID

[75] Inventors: Marc Piscitelli, Richmond Heights; Joseph S. Deucher, Lyndhurst; Robert E. Shroy, Jr., Willoughby, all of Ohio

[73] Assignee: Picker International, Inc., Cleveland, Ohio

[21] Appl. No.: 09/069,921

[22] Filed: Apr. 30, 1998

[51] Int. Cl.⁷ ........................................................ G21K 1/10
[52] U.S. Cl. ................................................ 378/154; 378/155
[58] Field of Search ...................................... 378/154, 155

[56] References Cited

U.S. PATENT DOCUMENTS

| | | |
|---|---|---|
| 4,039,841 | 8/1977 | Leighley . |
| 4,063,100 | 12/1977 | Williams . |
| 4,202,355 | 5/1980 | Loeffler . |
| 4,310,766 | 1/1982 | Finkenzeller . |
| 4,731,806 | 3/1988 | Takahata . |
| 5,056,128 | 10/1991 | Thompson . |
| 5,212,719 | 5/1993 | Virta et al. ........................ 378/155 |
| 5,241,578 | 8/1993 | MacMahon . |

FOREIGN PATENT DOCUMENTS 34 38 530 A1  4/1986  Germany .
1 597 077  9/1981  United Kingdom .

Primary Examiner—David P. Porta
Assistant Examiner—Pamela R. Hobden
Attorney, Agent, or Firm—Timothy B. Gurin; John J. Fry; Eugene E. Clair

[57] ABSTRACT

In an x-ray imaging system, an x-ray detector assembly includes an x-ray detector and a support assembly secured to the x-ray detector for supporting an antiscatter grid assembly. The x-ray detector preferably includes a matrix of crystal detectors. The support assembly includes a foam bezel having one or more magnets disposed therein. The antiscatter grid assembly includes an antiscatter grid secured to a metal frame. The one or more magnets disposed in the bezel are situated so as to align with the metal frame of the antiscatter grid assembly when the antiscatter grid assembly is coupled to the x-ray detector assembly. The strengths of the one or more magnets are such as to allow the antiscatter grid assembly to be removably secured to the x-ray detector assembly. Alternatively, the one or more magnets may be secured to the metal frame of the antiscatter grid assembly and corresponding metal plates may be placed in the support assembly.

19 Claims, 6 Drawing Sheets

MAGNETIC SUPPORT FOR REMOVABLE ANTISCATTER GRID

TECHNICAL FIELD

The present invention relates to the art of diagnostic imaging. It finds particular application in conjunction with x-ray imaging and will be described with particular reference thereto.

BACKGROUND OF THE INVENTION

In the medical imaging field, x-rays are often used to produce images of a patient for diagnostic purposes. The x-rays are generated within an x-ray tube and are directed through a patient or subject under examination to a detector assembly situated on an opposite side of the patient. Based on the intensity of the x-rays received by detectors within the detector assembly, an image indicative of the radiation attenuative characteristics of an object located between the tube and detector may be produced.

As x-rays pass through a body of a patient, the x-rays pass through tissue, bone, and other anatomy consisting of different densities all of which may cause some of the x-rays to scatter. If left unaccounted for, such scattered x-rays may degrade overall image quality. For this reason, antiscatter grids have been developed. An antiscatter grid is a device which attaches to the detector assembly and serves to prevent some or all of the scattered x-rays from reaching the detectors thereby providing for better image quality.

One known drawback to using an antiscatter grid is that it may also prevent some useful radiation from reaching the detectors. Thus, when using an antiscatter grid it is often times necessary to increase the dose of x-rays directed through the patient in order to ensure an image of sufficient quality may be obtained. Of course, if an antiscatter grid is not necessary to reduce the negative effects on image quality it would be desirable to remove the antiscatter grid so as to reduce the necessary dose of radiation to which the patient must be exposed. Thus, for example, in pediatrics and other fields requiring imaging of only a small volume, an antiscatter grid is typically not used. However, when imaging larger volumes, such as providing a fluoroscopic image during a needle biopsy of the liver, the antiscatter grid is very useful.

For this reason, antiscatter grids are typically mechanically secured to the detector assembly using a mechanism which allows for removal of the antiscatter grid when desired. Mechanisms used for detachment of the antiscatter grids include a quick release latches, fastening screws, and clips. One drawback to using such mechanisms is that there is often a need for the operator of the x-ray imaging device to utilize tools to remove the grid adding time and inconvenience to such a procedure. Even if a tool is not necessary, the operator is often wearing a glove to protect against exposure to radiation. Unfortunately, when wearing a glove there is typically reduced precision, dexterity, and tactile feedback which may be needed to manipulate small release devices. Additionally, antiscatter grid attachment mechanisms may present crevices and pockets which may trap fluids and increase the difficulty of disinfecting the x-ray imaging device.

Therefore, what is needed is a method and apparatus for coupling an antiscatter grid to a detector assembly which overcomes the shortfalls discussed above and others.

SUMMARY OF THE INVENTION

The present invention provides for an antiscatter grid to be magnetically coupled to a detector assembly. The detector assembly includes a bezel having one or more magnets disposed therein. The magnets are oriented along a perimeter of the bezel such that they align with a metal frame of the antiscatter grid. Magnetic attraction between the magnets and the metal frame of the antiscatter grid provide for a removably secured coupling of the antiscatter grid to the detector assembly. One or more magnets may alternatively or additionally be directly attached to the metal frame of the antiscatter grid. In such a case, the bezel includes corresponding metal plates to allow for attachment of the antiscatter grid to the detector assembly. In order to provide easy insertion and removal of the antiscatter grid from the bezel of the detector assembly, the bezel includes a pair of thumb holes.

In accordance with one aspect of the present invention, an x-ray imaging apparatus is provided. The x-ray imaging device includes an x-ray source capable of generating x-rays for imaging an object, an x-ray detector assembly situated substantially opposite the x-ray source for receiving the x-rays which have passed thought the object, and a means for reducing scatter reaching the x-ray detector assembly during detection of the x-rays. The means for reducing scatter is capable of magnetically coupling to the x-ray detector assembly.

In accordance with another aspect of the present invention, an antiscatter grid assembly is provided. The antiscatter grid assembly including a frame assembly having one or more magnets coupled to the frame assembly, and an antiscatter grid secured to the frame assembly.

In accordance with still another aspect of the present invention, an x-ray detector assembly is provided. The x-ray detector assembly including an x-ray detector, and an antiscatter grid support assembly secured to the x-ray detector, the support assembly including one or more magnets disposed therein.

In accordance with yet another aspect of the present invention, a method of removably securing an antiscatter grid assembly to an x-ray detector assembly is provided. The method includes the step of magnetically coupling the antiscatter grid assembly to the x-ray detector assembly.

One advantage of the present invention is that the magnetic coupling between the antiscatter grid and the detector assembly simplifies removal and reattachment of the antiscatter grid.

Another advantage of the present invention is that cleaning and disinfecting of the detector assembly may be simplified.

To the accomplishment of the foregoing and related ends, the invention then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE PREFERRED EMBODIMENTS

Figure 1:
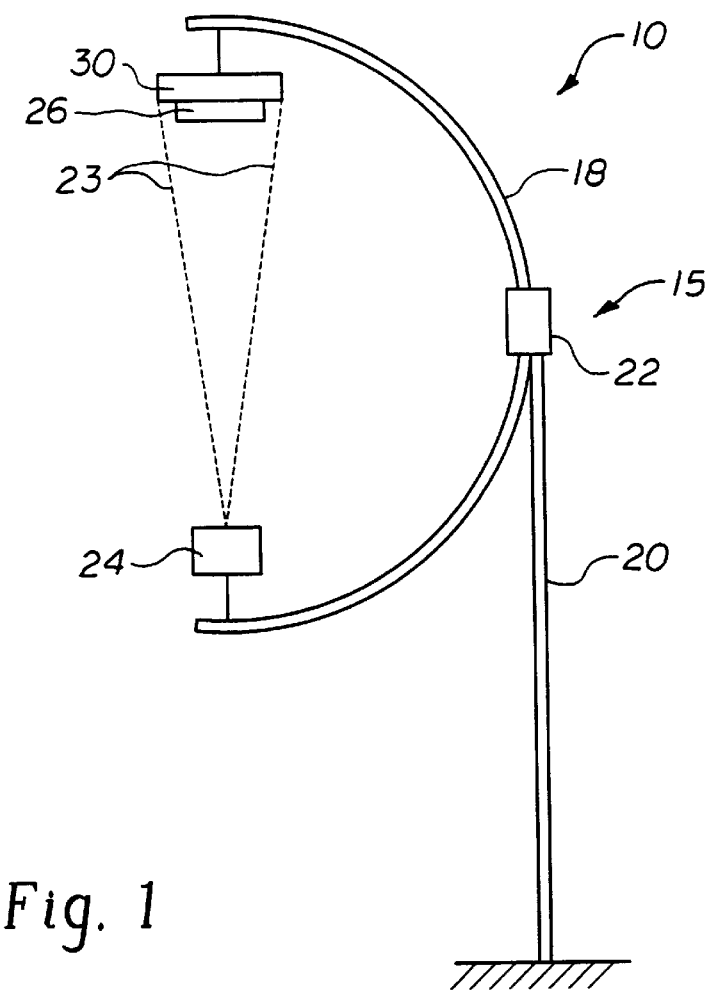
FIG. 1 is a representative side view of an x-ray imaging apparatus of the present invention.

With reference to FIG. 1, an x-ray imaging apparatus 10 includes a support structure 15 having a movable arm 18 shaped in the form of a "C". The movable arm 18 is rotatably coupled to a ground support leg 20 via a slidable connector 22. As electronic control panel 30 is secured to one end of the movable arm 18 and provides a user with the ability to control operations of the x-ray imaging apparatus 10. An x-ray source 24 is secured to an opposite end of the movable arm 18 and provides x-rays 23 for imaging of a patient or object 25. A x-ray detector assembly 26 is secured to the electronic control panel 30 for receiving the x-rays 23 and producing signals indicative of the strength of the x-rays received.

The detector assembly 26 preferably includes a flat panel silicon detector array. The array includes a sheet of scintillating material which emits a scintillation of light in response to incident radiation. An array of photodiodes disposed behind the scintillator generates an electrical signal indicative of the intensity of the incident radiation for each of a plurality of x,y positions in the array. Alternately, the detector assembly 26 may includes a so-called direct conversion array such as disclosed in U.S. Pat. Nos. 5,331,179 and 5,319,206 to Lee. These detectors convert the incident radiation directly to electrical charge using a selenium photoconductor layer on top of a microcapacitor matrix.

A patient or other object to be imaged is situated on a patient support (not shown) between the x-ray source 24 and the detector assembly 26. It will be appreciated that the x-ray imaging apparatus 10 may also be part of a computed tomography (CT) imaging apparatus (not shown).

The detector assembly 26 is coupled to image reconstruction circuitry 28 which serves to reconstruct an image of the object 25 based on the position and intensity of the detected x-rays 23 as is known in the art. The reconstructed image may then be displayed on a video monitor 29 or otherwise be stored for later retrieval. If used to produce fluoroscopic images, the detector 26 and reconstruction circuitry combine to produce a repeatedly updated image which is useful for observing a dynamic function, guiding a procedure, searching through a body section, or the like. If used to produce radiographic images, one or more still images are generated.

Figure 2:
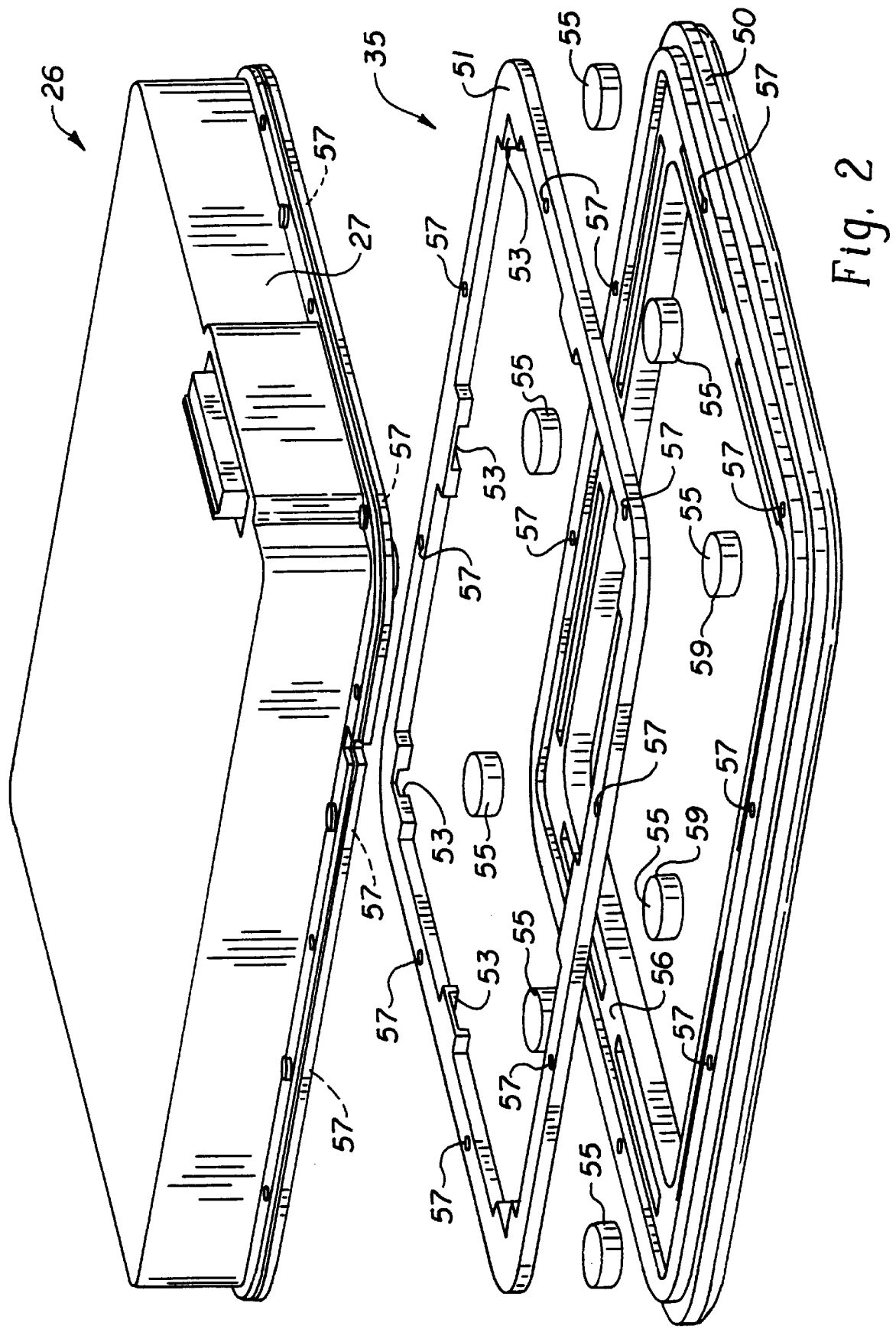
FIG. 2 is an exploded isometric view of a detector assembly of the present invention.

Referring now to FIG. 2, an exploded view of the detector assembly 26 of the present invention is shown. As shown, the detector assembly 26 includes a flat panel detector 27 and a support assembly 35. The support assembly 35 includes a bezel 50, a sub-frame 51, and magnets 55. The bezel 50 is made of a soft durable material, such as a urethane foam 90 (FIG. 5), and aids in sealing the flat panel detector 27 from light, air, and fluids which may otherwise deleteriously effect image quality and sterility of the flat panel detector 27. The foam 90 also helps form a seal against bio-hazardous fluids which may be introduced at or near the flat panel detector 27. Disposed in the bezel 50 is a series of puck-shaped magnets 55. Although the magnets 55 are shown above the bezel 50 in the exploded view of FIG. 2, it will be appreciated that the bezel 50 is actually molded about the magnets 55. This may be seen more clearly below with reference to FIG. 5 wherein the magnets 55 are shown actually situated within the soft urethane foam 90 of bezel 50. In the present invention the support assembly 35 includes eight magnets 55, however it will be appreciated that any number of suitable magnets may be used. Each magnet 55 of the present embodiment is approximately ¾ inch in diameter and ¼ inch in height. Further, each magnet 55 has a strength, or pulling force, of approximate eight pounds. As is discussed in more detail below, the combined strength of the magnets 55 is sufficient to support an antiscatter grid assembly 45 through the bezel 50 while still allowing for easy removal by a user. Of course, other suitable sizes, shapes, and strengths for the magnets 55 may alternatively be used.

Figure 3:
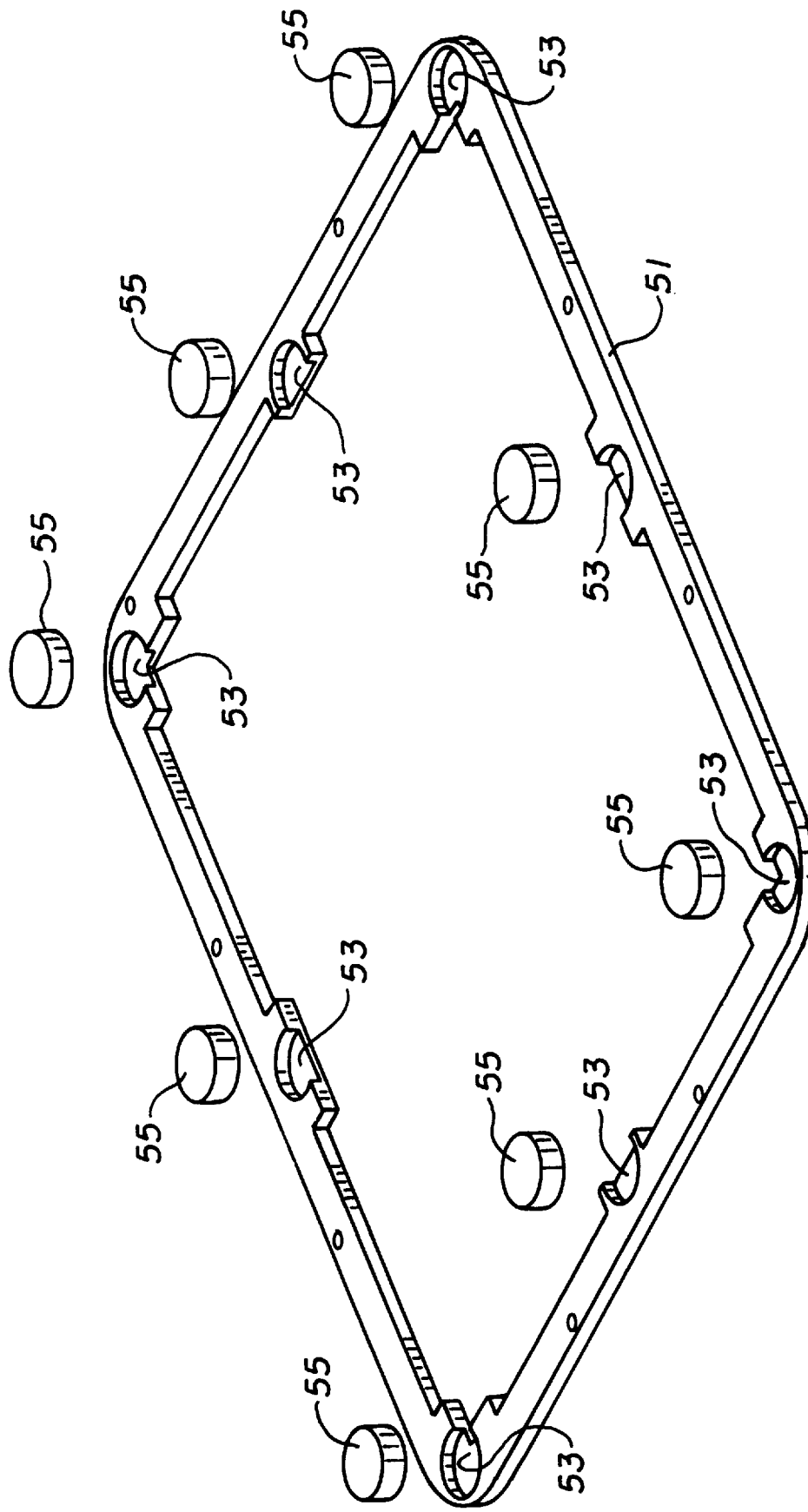
FIG. 3 is an isometric view of a sub-frame of the detector assembly of FIG. 2.

The sub-frame 51 is made of a metal such as steel and provides support for bezel 50. As best seen in FIG. 3, the sub-frame 51 includes a magnet receiving groove 53 corresponding to each magnet 55. The magnet receiving grooves 53 provide added security to placement of the magnets about the periphery of the bezel 50.

Referring again to FIG. 2, the flat panel detector 27 is coupled to the support assembly 35 by way of a plurality of screws (not shown) which are threaded through aligned screw apertures 57 in the bezel 50, the sub-frame 51 and the flat panel detector 27. The screws are inserted through a bottom surface 91 of the bezel and are threaded through both the sub-frame 51 and flat panel detector 27.

Figure 4:
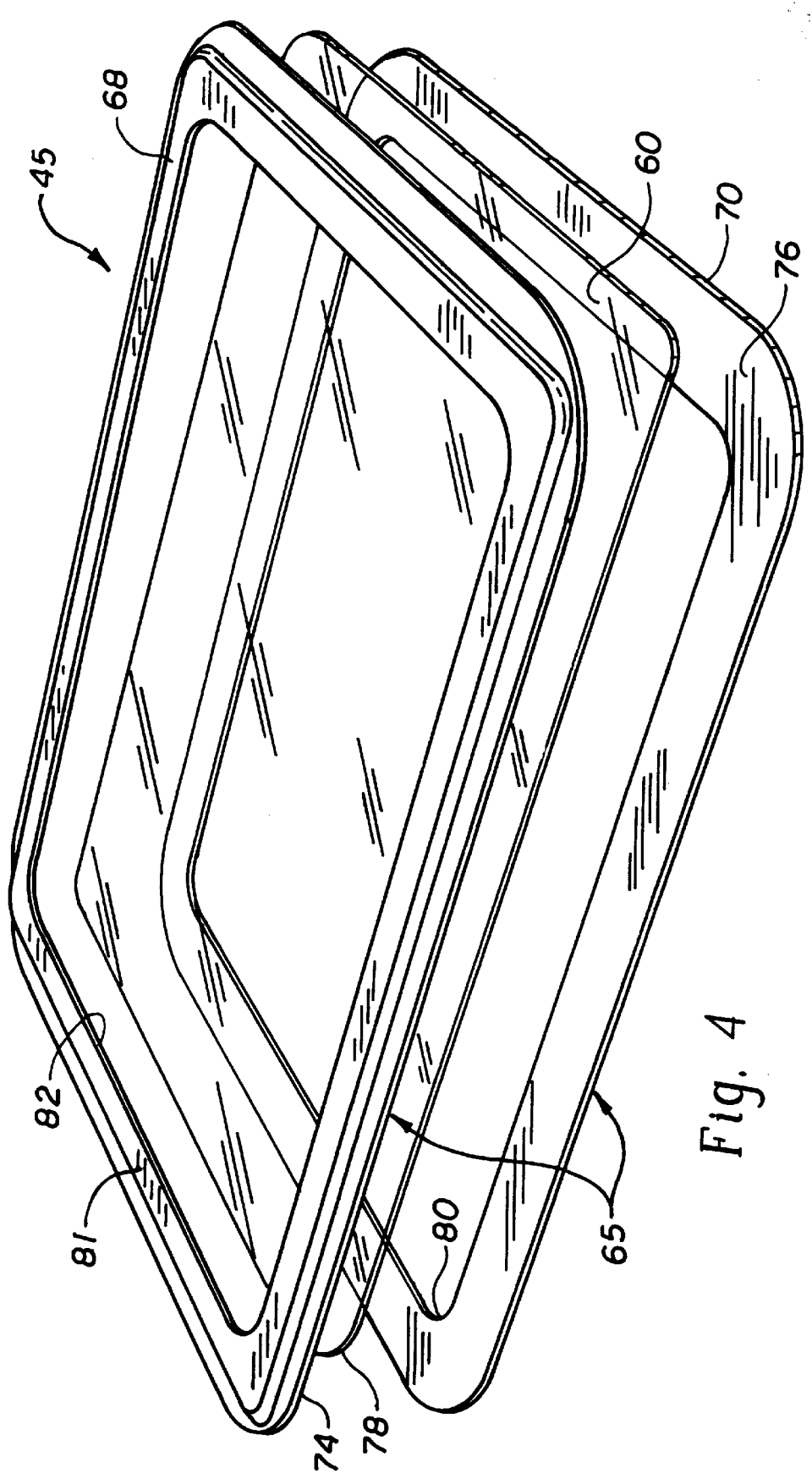
FIG. 4 is an exploded isometric view of an antiscatter grid assembly of the present invention.

Referring now to FIG. 4, an exploded view of the antiscatter grid assembly 45 is shown. The antiscatter grid assembly 45 includes an antiscatter grid 60 which in the present embodiment is made of a carbon fiber and serves to prevent stray radiation from reaching the detectors (not shown). An antiscatter grid which may be used in the present embodiment is, for example, of a type commercially available from Smit Rotogen in the Netherlands. The antiscatter grid assembly 45 further includes a frame assembly 65 having an upper frame 68 and a lower frame 70. The upper frame 68 and the lower frame 70 are both made of a metal such as steel, and together serve to sandwich the antiscatter grid 60 therebetween. More specifically, a lower surface 74 of the upper frame 68 is bonded to an upper surface 76 of the lower frame 70 with the antiscatter grid 60 sandwiched between using an epoxy resin. The epoxy resin provides a secure, permanent connection which also bonds with the carbon fiber of the antiscatter grid 60. Of course other bonding methods which would not deleteriously effect the performance of the antiscatter grid 60 may also be used. An outer periphery 78 of the antiscatter grid 60 is slightly larger than an inner periphery 80 of the lower frame 70 such that the sandwiched antiscatter grid 60 may be supported by, and rest on, the lower frame 70. Further, to ensure proper alignment of the antiscatter grid 60, the upper frame 68 includes a raised portion 81 along its inner periphery 82 with a height just slightly larger than a height of the antiscatter grid 60 so as to allow situation of the antiscatter grid 60 therein. The frame assembly 65 serves to provide a magnetic interface for the antiscatter grid assembly 45 to couple to the bezel 50 (FIG. 2) and also helps protect the antiscatter grid 60 from damage in the event it is dropped or otherwise mishandled.

Figure 5:
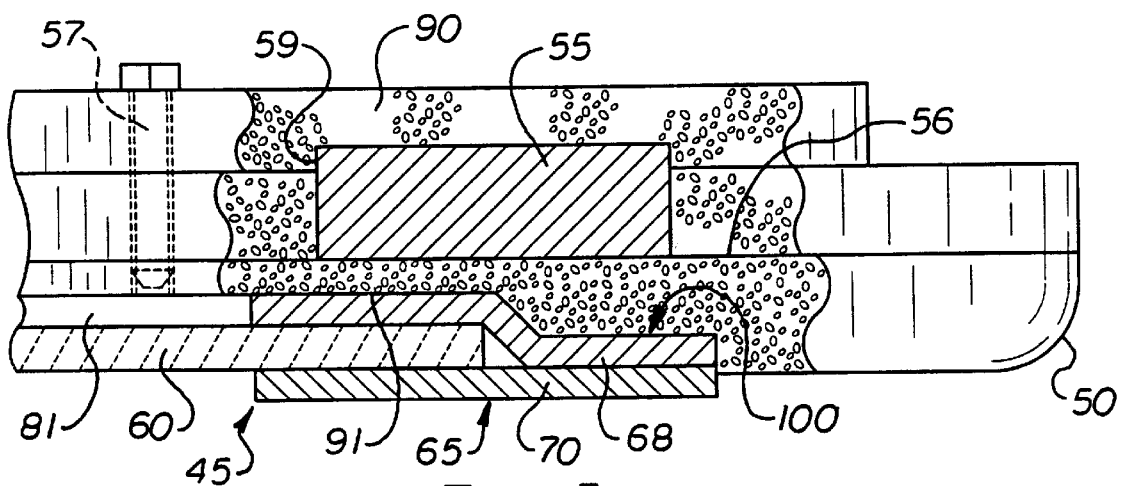
FIG. 5 is a partial cross sectional enlarged side view of a bezel of the detector assembly of FIG. 2 supporting the antiscatter grid assembly of FIG. 4.

Turning now to FIG. 5, a more detailed view of the disposition of the magnets 55 within the urethane foam 90 of the bezel 50 having is shown along with the antiscatter grid assembly 45 coupled thereto. More specifically, the magnet 55 is shown to be disposed within the urethane foam 90 of the bezel 50 in a manner sufficiently close to the bottom surface 91 of the bezel 50 so as to allow magnetic forces of the magnet 55 to support the antiscatter grid assembly 45 placed in proximity thereto. A top portion 59 of each magnet 55 protrudes upward from a inner surface 56 of the bezel 50 (see FIG. 2) such that the magnet receiving grooves 53 in the sub-frame 51 fit over the magnet 55.

Figure 6:
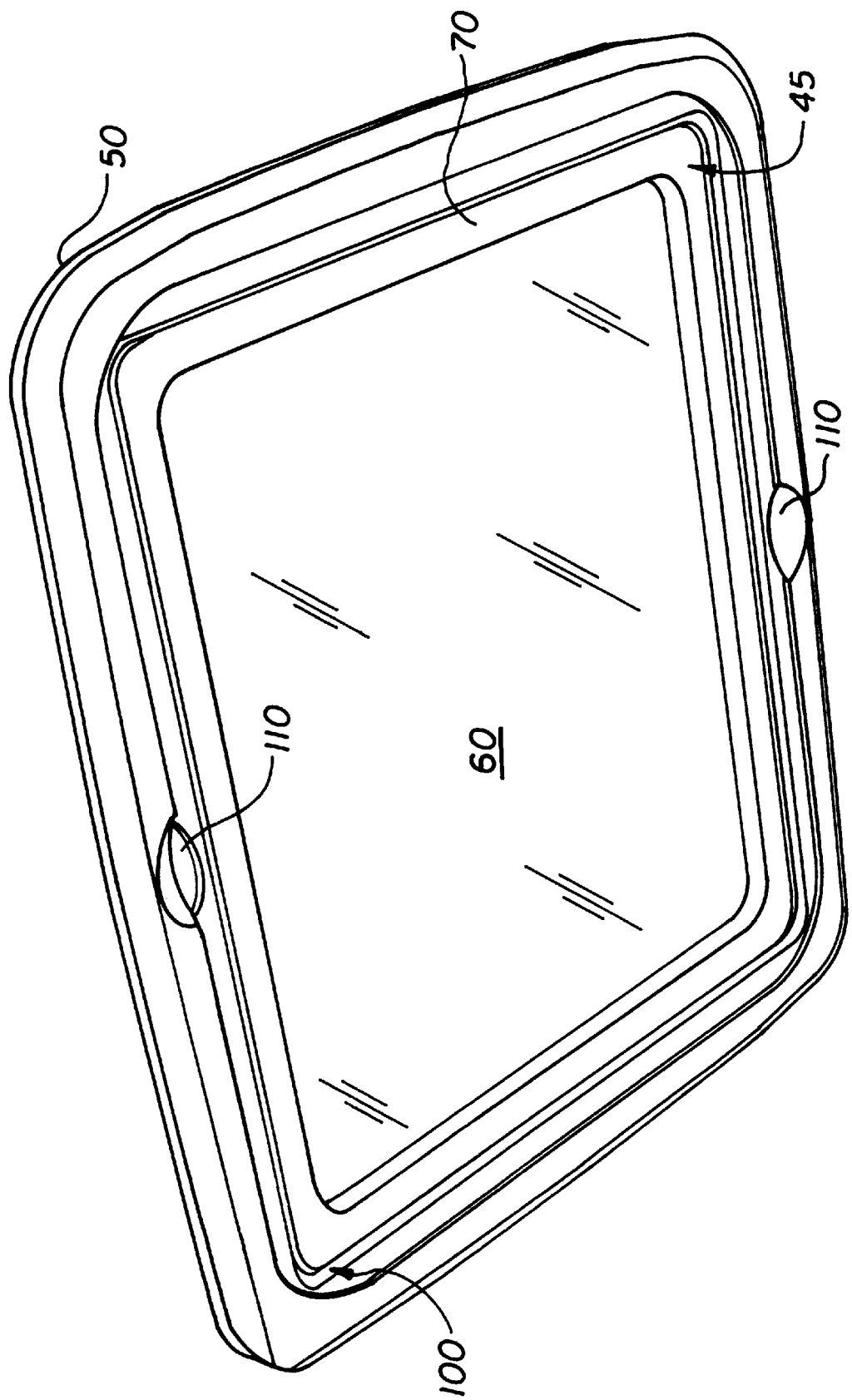
FIG. 6 is an isometric view of the antiscatter grid coupled to the detector assembly of the present invention.

As best seen in FIGS. 5 and 6, a bottom portion of the bezel 50 defines a recessed chamber 100 which is sized and shaped to snugly fit the antiscatter grid assembly 45. A pair of thumb holes or thumb indents 110 in the bezel 50 defined along opposite sides of the recessed chamber 100 provides for easy insertion are removal of the antiscatter grid assembly 45 from the bezel 50 of the detector assembly 26 (FIG. 1). The thumb holes 110 may be sized to accommodate users who may have gloves on their hands, for example. Although two thumb holes 110 are disclosed in the present embodiment, it will be appreciated that one or more thumb holes of various sizes may alternatively be used.

In operation, the antiscatter grid assembly 45 may be easily inserted and removed from the bezel 50 of the detector assembly 26. Insertion of the antiscatter grid assembly 45 may be accomplished by placing the antiscatter grid assembly 45 within a close proximity of the recessed chamber 100 of the bezel 50. As the antiscatter grid assembly 45 is moved close to the recessed chamber 100, the magnets 55 and the upper frame 68 of the metal frame assembly 65 sufficiently attract such that the antiscatter grid assembly 45 couples to the bezel 50 with no further action on the part of the user. In order to remove the antiscatter grid assembly 45, the user may place any one of his/her fingers, for example, into the oppositely spaced thumb holes 110 and direct the antiscatter grid assembly 45 away from the recessed chamber 100. As the grid 45 begins to move away from the bezel 50, and hence the magnets 55, the antiscatter grid assembly 45 becomes fully removed and independent of the bezel 50. Thus, the present invention provides for a simple and efficient manner to couple the antiscatter grid 60 to the detector assembly 26 which requires no additional mechanical clips, joints or fasteners. Further, because there are no additional mechanical connections and crevices, the present invention provides for a design which allows the detector assembly 26 to be easily cleaned for disinfection purposes.

Figure 7:
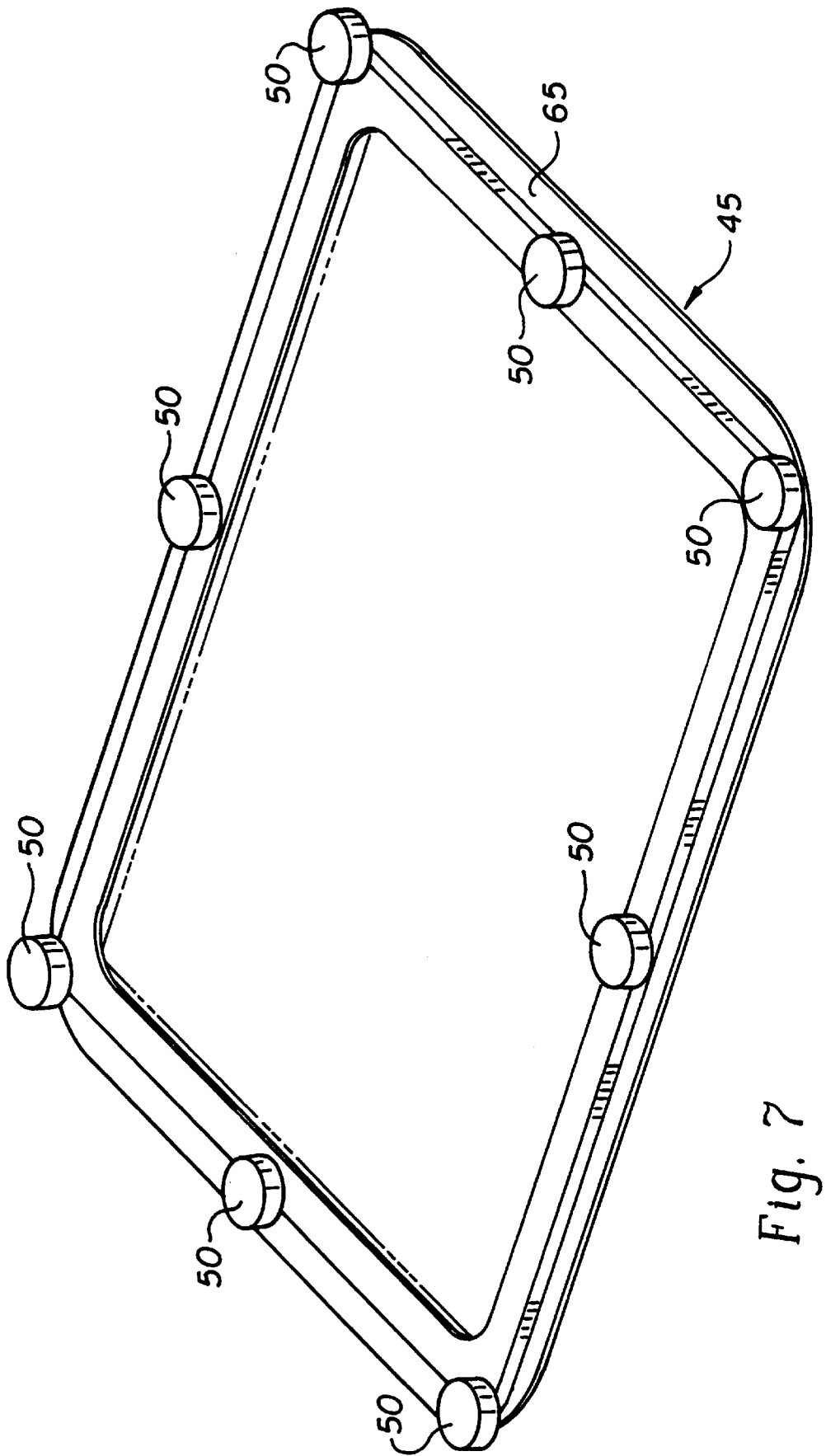
FIG. 7 is an isometric view of a grid assembly in accordance with an alternative embodiment of the present invention.

Referring now to FIG. 7, an alternative embodiment of the present invention is shown. In this embodiment the metal frame assembly 65 of the antiscatter grid assembly 45 is shown to have the magnets 55 secured thereon. The magnets 55 may be secured to the metal frame assembly 65 using an epoxy other suitable adhesive. Alternatively, the magnets 55 may be mechanically secured to the antiscatter grid assembly 45. In order to couple the antiscatter grid assembly 45 of the present embodiment to the bezel 50 of the detector assembly 26, the bezel 50 includes metal discs made of steel, for example, in place of the magnets 55. Thus, when the magnets 55 situated on the antiscatter grid assembly 45 are brought into close proximity to the metal plates disposed in the bezel 50, a magnetic coupling allows the antiscatter grid assembly 45 to become attached to the bezel 50. It will also be appreciated, that the bezel 50 and the antiscatter grid assembly 45 may both have magnets 55 coupled or disposed thereon. In such a case, the opposing component provides a metal surface such that the metal surface aligns with the opposing magnet 55 on the other component when the two components are joined.

While the anti-scatter grid has been described in connection with a c-arm system which is particularly well-suited for interventional procedures, it may also be used in conjunction with radiographic or fluoroscopic tables, in CT scanners, or the like.

The invention has been described with reference to the preferred embodiments. Obviously, modifications and alterations will occur to others upon reading and understanding the preceding detailed description. It is intended that the invention be construed as including all such modifications and alterations.

What is claimed is:

1. An x-ray imaging apparatus comprising:

an x-ray source capable of generating x-rays for imaging an object;

an x-ray detector assembly situated substantially opposite the x-ray source for receiving the x-rays which have passed through the object, the x-ray detector assembly including a bezel;

one or more magnets at least in part disposed within the bezel; and means for reducing scatter reaching the x-ray detector assembly during detection of the x-rays, said means being magnetically attached to the x-ray detector assembly.

2. The apparatus of claim 1, wherein the means for reducing scatter is an antiscatter grid assembly.

3. The apparatus of claim 2, wherein the antiscatter grid assembly includes an antiscatter grid supported within a metal frame.

4. The apparatus of claim 3, wherein the one or more magnets are disposed about a periphery of the x-ray detector assembly, the one or more magnets positioned so as to align with the metal frame of the antiscatter grid assembly when the antiscatter grid assembly is attached to the x-ray detector assembly.

5. The apparatus of claim 4, wherein the x-ray detector assembly includes a support assembly secured to an x-ray detector, and the antiscatter grid assembly attaches to the support assembly.

6. The apparatus of claim 5, wherein the bezel is comprised of foam.

7. The apparatus of claim 6, wherein the bezel includes at least one thumb indent for removing an antiscatter grid assembly coupled to the support assembly.

8. The apparatus of claim 2, wherein the antiscatter grid assembly includes an antiscatter grid supported within a frame having one or more magnets mounted thereto.

9. The apparatus of claim 8, wherein the x-ray detector assembly includes one or more metal plates disposed about a periphery of the x-ray detector assembly, the one or more metal plates positioned so as to align with the one or more magnets of the antiscatter grid assembly when the antiscatter grid assembly is attached to the x-ray detector assembly.

10. The apparatus of claim 1, further comprising a movable C-arm wherein the x-ray source is mounted to one end of the C-arm and the x-ray detector assembly is mounted to an opposite end of the C-arm.

11. An antiscatter grid assembly comprising:

a frame;

one or more magnets mounted around a periphery of the frame, whereby the magnets are for magnetically securing the grid assembly to a detector assembly; and an antiscatter grid secured to the frame.

12. The antiscatter grid assembly of claim 11, wherein frame includes an upper frame portion and a lower frame portion and the antiscatter grid is disposed between the upper frame and the lower frame portion.

13. The antiscatter grid assembly of claim 12, wherein the upper frame portion is secured to the lower frame portion using an epoxy resin.

14. An x-ray detector assembly, comprising:
an x-ray detector; and
an antiscatter grid support assembly secured to the x-ray detector, the support assembly including a bezel and one or more magnets are at least in part disposed therein.

15. The x-ray detector assembly of claim 14, wherein the bezel is comprised of foam.

16. The apparatus of claim 15, wherein the bezel includes at least one thumb indent for removing an antiscatter grid assembly coupled to the support assembly.

17. A method of removably securing an antiscatter grid assembly to an x-ray detector assembly, the method comprising the steps of:

aligning the antiscatter grid assembly with a recessed chamber in a bezel of the x-ray detector assembly; and magnetically attaching the antiscatter grid assembly in the recessed chamber of the bezel of the x-ray detector assembly.

18. The method of claim 17, wherein the antiscatter grid assembly includes an antiscatter grid supported within a metal frame.

19. The apparatus of claim 18, wherein the x-ray detector assembly includes one or more magnets disposed about a periphery of the x-ray detector assembly, the one or more magnets positioned so as to align with the metal frame of the antiscatter grid assembly when the antiscatter grid assembly is coupled to the x-ray detector assembly.

* * * * *

UNITED STATES PATENT AND TRADEMARK OFFICE
CERTIFICATE OF CORRECTION

PATENT NO. : 6,064,720

DATED : May 16, 2000

INVENTOR(S) : Marc Piscitelli, Joseph S. Deucher, Robert E. Shroy, Jr.

It is certified that error appears in the above-identified patent and that said Letters Patent is hereby corrected as shown below:

column 1, the sentence –The present application claims priority to U.S. Provisional Application Serial Number 60/066,600 filed on November 26, 1997– should be inserted as the first sentence following the title.

Signed and Sealed this

Twenty-second Day of May, 2001

*Attest:*

NICHOLAS P. GODICI

*Attesting Officer*     *Acting Director of the United States Patent and Trademark Office*